United States Patent [19]

Morishita

[11] Patent Number: 4,976,151
[45] Date of Patent: Dec. 11, 1990

[54] METHOD AND DEVICE FOR DETECTING BLOCKED CONDITION IN A TUBE OF A LIQUID INFUSION PUMP

[75] Inventor: Masakazu Morishita, Wakayama, Japan

[73] Assignee: Sharp Kabushiki Kaisha, Osaka, Japan

[21] Appl. No.: 494,838

[22] Filed: Mar. 15, 1990

Related U.S. Application Data

[63] Continuation-in-part of Ser. No. 351,270, May 11, 1989, abandoned, which is a continuation of Ser. No. 154,052, Feb. 9, 1988, abandoned.

[30] Foreign Application Priority Data

Feb. 17, 1987 [JP] Japan .................................. 62-22504

[51] Int. Cl.[5] ................................................ G01L 9/10
[52] U.S. Cl. ........................................ 73/730; 73/728; 336/30
[58] Field of Search ...................... 73/730, 728; 336/30

[56] References Cited

U.S. PATENT DOCUMENTS 3,698,249  10/1972  Weaver ................................. 73/730
4,702,675  10/1987  Aldrovandi ........................... 73/730

Primary Examiner—Donald O. Woodiel
Attorney, Agent, or Firm—Flehr, Hohbach, Test, Albritton & Herbert

[57] ABSTRACT

A detector for a blocked condition in a tube of a liquid infusion pump includes a moveable shaft which is kept in contact with the outer wall of a flexible tube for transporting a liquid therethrough and moves according to the changes in the outer diameter of the tube corresponding to changes in the internal pressure of the liquid. A magnet core is affixed to this shaft and affects the inductance of a solenoid coil which is affixed at a fixed position. A blocked condition in the tube is detected by monitoring the change in the inductance of this coil.

8 Claims, 1 Drawing Sheet

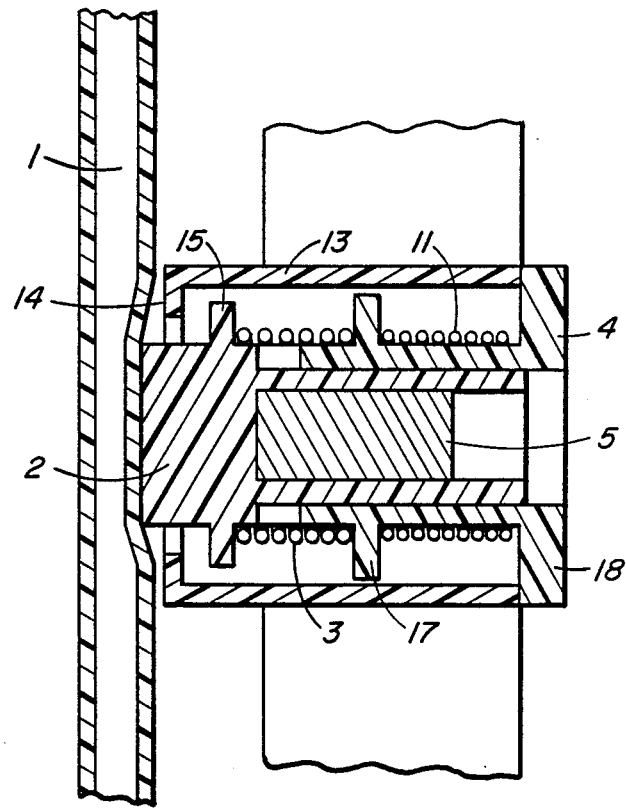
FIG._1.
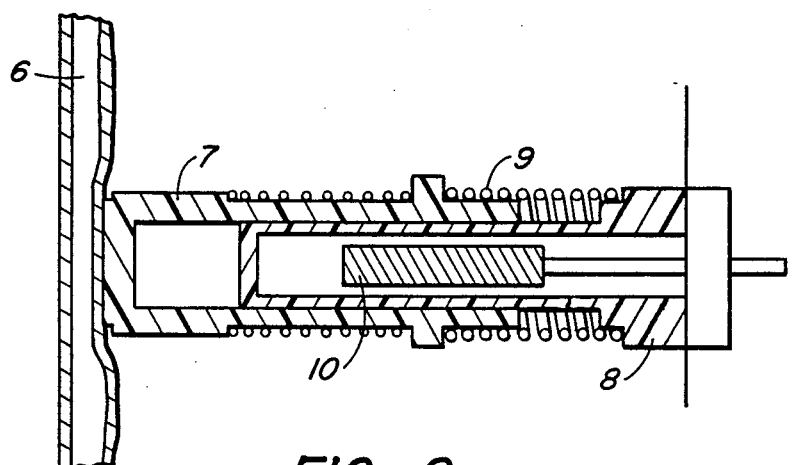
FIG._2.
(PRIOR ART)

METHOD AND DEVICE FOR DETECTING BLOCKED CONDITION IN A TUBE OF A LIQUID INFUSION PUMP

This is a continuation-in-part of application Ser. No. 351,270 filed May 11, 1989, now abandoned, which is a continuation of application Ser. No. 154,052 filed Feb. 9, 1988, now abandoned.

BACKGROUND OF THE INVENTION

This invention relates to a method and device for detecting a blocked condition in a tube of a liquid infusion pump.

A device for this purpose structured as shown in FIG. 2 has been known. In FIG. 2, numeral 6 indicates a flexible tube for. transporting a liquid therethrough and a mobile coil 7 is disposed in contact with the outer wall of this flexible tube 6 When the internal pressure of this tube 6 changes, the external diameter of the tube 6 also changes correspondingly and the coil 7 is displaced accordingly. A fixed axis 8 is inserted inside the coil 7 such that there is a coaxial relationship therebetween. A biasing spring 9 is provided with one end attached to the fixed axis 8 such that the coil 7 is constantly pressed against the tube 6. A magnet core 10 is disposed inside the fixed axis 8 such that there will be a change in inductance if the coil 7 moves along the axis 8 and this is how a change in the external diameter of the tube 6 is detected. With a detector thus structured, however, the lead wires of the coil 7 are likely to break because the coil 7 keeps moving all the time.

SUMMARY OF THE INVENTION

It is therefore an object of the present invention to provide an improved method and device for detecting a blocked condition in a tube of a liquid infusion pump which measures changes in inductance of a coil such that the lead wires of the coil are not likely to break easily.

The above and other objects of the present invention are achieved by providing a detector having a magnet core attached to a mobile member in contact with the external wall of a flexible tube through which the liquid is pumped and a coil disposed at a fixed position such that the motion of the magnet core is detected by the change in inductance of this fixed coil.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings:

FIG. 1 is a drawing which shows the structure of a detector embodying the present invention, and FIG. 2 is a drawing which shows the structure of a prior art detector for a blocked condition in a tube of a liquid infusion pump.

DETAILED DESCRIPTION OF THE INVENTION

In what follows, the structure of a detector embodying the present invention for a blocked condition in a tube of a liquid infusion pump is explained with reference to FIG. 1 wherein numeral 1 indicates a flexible (liquid-transporting) tube connected to a bag (not shown) containing a liquid to be infused. The pumping of the liquid is effected by a pump head (not shown) peristaltically compressing this flexible tube 1. Operation of such a pump is well known and will not be explained here.

At the time of an infusion, a predetermined amount of liquid may have to be supplied through the tube 1, for example, to the body of a patient. In such an application, a blocked condition in the tube 1 that may stop the supply of liquid must be carefully avoided.

According to the present invention, there is provided a movable shaft 2 which has an outwardly protruding flange 15 and has one end in contact with the outer wall of the flexible tube 1 for detecting a blocked condition therein. The shaft 2 is made, for example, of synthetic resin and is adapted to move slidably inside and along a cylindrical inner wall of a bobbin 4 in response to a change in the outer diameter of the tube 1. The bobbin 4 is made of a non-magnetic material such as synthetic resin and is provided with an outwardly protruding end flange 18 at its end distal from the tube 1 and another outwardly protruding flange 17 at a position between the end flange 18 and the flange 15 of the shaft 2. A tubular cover piece 13 having an inwardly protruding flange 14 at its end proximal to the tube 1 is attached to the end flange 18 of the bobbin 4, substantially entirely enveloping the bobbin 4 as well as the shaft 2 inside. This inwardly protruding flange 14 serves as a stopper, preventing the outer wall of the tube 1 from moving in the direction of the cover piece 13 by any change of the pressure inside the tube 1. The cover piece 13 is rigidly supported by the main structure of the detector so as not only to remain stationary itself but also to keep the bobbin 4 stationary independently of the motion of the shaft 2 caused by a change in the diameter of the tube 1. A coil spring 3 is provided between the outwardly protruding flanges 15 and 17 respectively of the shaft 2 and the bobbin 4 so as to apply a biasing force on the movable shaft 2 in the direction towards the tube 1. A solenoid coil 11 is supported by the bobbin 4 between the two flanges 17 and 18 thereof so as also to remain stationary independent of the motion of the shaft 2. As can be seen in FIG. 1, the solenoid coil 11, the shaft 2 and the coil spring 3 are coaxially disposed with respect to one another. A core 5 made of a permanent magnet or a ferromagnetic material is secured inside the shaft 2 such that the inductance of the solenoid coil 11 is affected by this core 5.

As described above, one of the end surfaces (front end surface) of the shaft 2 is pressed by the spring 3 against the outer wall of the tube 1 such that changes in the outer diameter of the tube 1 caused by those in its internal pressure are sensed and measured as the changes in its relative distance to solenoid coil 11. Since the magnet core 5 secured inside the shaft 2 is moved with the shaft 2 according to the present invention, the changes in the internal pressure of the tube 1 can be measured as changes in the inductance of the solenoid coil 11. Since the solenoid coil 11 itself is at a fixed position and does not move, however, lead wires connected to the solenoid coil 11 do not break.

The changes in the inductance of the solenoid coil are converted into the frequency of oscillation which is inputted to a large scale integration chip (not shown) which serves to determine whether a blocked condition exists or not in the tube 1 on the basis of the data on the changes in the outer diameter of the tube 1. If it is judged that the tube 1 is blocked, a buzzer is sounded or otherwise a warning signal is outputted.

In summary, the detector according to the present invention is characterized as detecting the changes in the internal pressure of a flexible tube (or, more precisely, the internal pressure of the liquid being transported through this tube) by monitoring the changes in the inductance of a stationary solenoid coil caused by the positional changes of a magnet core affixed to a shaft which is in contact with the outer wall of the tube and moves therewith. Since the coil itself does not move with the changes in the internal pressure of the tube, its lead wires do not break, unlike those in conventional detectors, and a blocked condition in a tube can be more reliably monitored by a detector of the present invention.

The foregoing description of a preferred embodiment of the invention has been presented for purposes of illustration and description. It is not intended to be exhaustive or to limit the invention to the precise form disclosed. Any modifications and variations that may be apparent to a person skilled in the art are intended to be within the scope of this invention.

What is claimed is:

1. A detector for a blocked condition in a tube of a liquid infusion pump comprising
    a tubular member, having a center flange and a back flange,
    a shaft having one end in contact with the outer wall of a flexible tube for transporting a liquid therethrough by a liquid infusion pump, said shaft having a front flange and being slidably movable through said tubular member, said tubular member being secured so as to remain stationary independently of the motion of said shaft,
    a magnet core affixed to said shaft,
    a solenoid coil disposed around said tubular member and secured to and extending between said center flange and said back flange, said magnet core being sufficiently near said coil such that the inductance of said coil is affected by said magnet core, the inductance of said coil changing by a movement of said magnet core,
    a coil spring disposed around said shaft and secured to and compressed between said center flange of said tubular member and said front flange of said shaft, and
    a cover piece attached to said back flange of said tubular member and substantially entirely enclosing said tubular member, said cover piece having an inwardly protruding flange serving as a stopper for said flexible tube,
    said detector being capable of detecting a blocked condition in said flexible tube by detecting a change in the inductance of said coil.

2. The detector of claim 1 wherein said shaft and said solenoid coil are coaxial with respect to each other.

3. A method of detecting a blocked condition in a tube of a liquid infusion pump, said tube having an outer wall which moves according to a change in pressure inside said tube, said method comprising the steps of
    providing a tubular member affixed to remain stationary independently of movements of said outer wall of said tube, said tubular member having a center flange and a back flange, a solenoid coil being disposed around said tubular member and being secured to and between said center flange and said back flange,
    attached a magnet core to a shaft which is in contact with said outer wall of said tube so as to be movable and to cause said magnet core to move with said outer wall longitudinally along said solenoid coil while remaining near said solenoid coil such that the inductance of said solenoid coil is affected by said magnet core, and
    detecting a blocked condition in said tube by detecting a change in the inductance of said solenoid coil.

4. The method of claim 3 wherein said shaft is kept in contact with said outer wall of said tube by means of biasing means.

5. The method of claim 4 wherein said biasing means comprises a spring.

6. The method of claim 5 wherein said shaft has a front flange formed thereon and said spring is compressed between said front flange of said shaft and said center flange of said tubular member.

7. The method of claim 3 wherein said shaft and said solenoid coil are coaxial with respect to each other.

8. The method of claim 3 further comprising the step of providing a tubular cover piece which is attached to said back flange of said tubular member and substantially entirely encloses said tubular member and said shaft.

* * * * *